United States Patent [19]

Proksch

[11] Patent Number: 5,055,412
[45] Date of Patent: Oct. 8, 1991

[54] FACTOR SENSITIVE REAGENT FOR TESTING OF BLOOD COAGULATION CONTAINING ELLAGIC ACID AND DIVALENT METAL IONS AND METHOD OF MAKING THE SAME

[76] Inventor: Gary J. Proksch, 7764 N. Hoover, Indianapolis, Ind. 46260

[21] Appl. No.: 326,381

[22] Filed: Mar. 21, 1989

[51] Int. Cl.$^5$ .............................................. G01N 33/86
[52] U.S. Cl. ......................................... 436/69; 435/13
[58] Field of Search .............................. 436/69; 435/13

[56] References Cited

U.S. PATENT DOCUMENTS 3,486,981 12/1969 Speck ..................................... 435/13
4,732,860 3/1988 Bartl et al. ......................... 435/13 X

FOREIGN PATENT DOCUMENTS 2915310 10/1980 Fed. Rep. of Germany ........ 435/13

OTHER PUBLICATIONS

*Activation of Intrinsic Blood Coagulation by Ellagic Acid: Insoluble Ellagic Acid–Metal Ion Complexes are the Activating Species,* Biochemistry (1981), 20, 7258–7265.
Ratnoff et al, J. Lab. Clin. Med., vol. 63, No. 3, pp. 359–377, Mar. 1964.

*Primary Examiner*—Robert J. Hill, Jr.
*Attorney, Agent, or Firm*—Woodard, Emhardt, Naughton, Moriarty & McNett

[57] ABSTRACT

The present invention involves a partial thromboplastin time test reagent which is factor sensitive depending upon the selected reagent constituents. A method for peparing such reagent is also disclosed. The present invention further involves a procoagulant precursor reagent and a method of making it. The factor sensitive reagent is of exceptional stability enabling more precise partial prothrombin time measurements. The reagents contain ellagic acid or an ellagic acid salt and divaent metal ions in a specific molar ratio relative to the ellagic acid or ellagic acid salt.

53 Claims, No Drawings

FACTOR SENSITIVE REAGENT FOR TESTING OF BLOOD COAGULATION CONTAINING ELLAGIC ACID AND DIVALENT METAL IONS AND METHOD OF MAKING THE SAME

BACKGROUND OF THE INVENTION

This invention relates to the field of blood coagulation testing, specifically to reagents useful in measuring various coagulation factors and a method for the preparation of such reagents.

Effective medical treatment of certain patients requires the measurement of the blood's clotting ability. In general, the blood coagulation process depends upon the presence of interactive blood components which cause blood to form a gel. The first stage of coagulation is formation of blood thromboplastin. Several intrinsic blood constituents interact to form blood thromboplastin, one of which is platelets. This is followed by the conversion of prothrombin to thrombin, a process aided by the now present blood thromboplastin. Third, thrombin acts on fibrinogen present in the blood to form fibrin, an insoluble plasma protein. Fibrin, by its insoluble nature, forms a clot. Depending upon the site of clotting, step one above may be obviated. For example, tissue thromboplastin is continuously present in nearly all body tissues and is also active in prothrombin conversion.

If any one of the factors essential to clotting is absent, or present in insufficient quantity, the clotting ability of blood is seriously impaired. The time for the clotting process to take place is measured as an indicator. The clinician, once armed with the knowledge that the patient cannot form clots in normal time, can adjust his treatment program accordingly. Postoperatively, healing may be hindered by low clotting time. Therefore, postoperative treatment may be specially tailored once low clotting time is realized. As a diagnostic tool, absence or low incidence of a factor necessary to clotting is useful in determining a patient's disease. In this regard, a factor sensitive reagent is highly desirable.

In a typical test procedure, blood is withdrawn from the human body and centrifuged to remove the platelets and blood cells. The supernatant plasma is withdrawn and mixed with a partial thromboplastin time reagent containing an activator and a platelet substitute. After a period the clotting factors are activated. After the addition of calcium, the solution is put into a cuvette and placed in a spectrophotometer for measuring the change in absorbency. Alternatively formation of a clot is observed directly by the human eye.

There are a variety of commercially available reagents for measuring partial thromboplastin. It is known that certain ellagic acid solutions are successful contact activators. Thus, ellagic acid forms an effective activated cephaloplastin reagent. Several formulations utilizing ellagic acid, generally at 100 micromolar concentration, are commercially available, for example, Actin* (available from American Dade, division of Baxter Travenol Diagnostics, Inc. of Miami, Fla.). These commercially available cephaloplastin reagents also include a phospholipid, typically a cephalin, as a platelet substitute. Further, some of these reagents contain metal ions at various concentration ratios to ellagic acid. The metal ion concentration ratios from some of these activated partial thromboplastin time reagents have been determined using atomic absorbtion spectroscopy. The following table summarizes this data:

| Ion | Activated Thrombofax | Actin | Actin-FS |
|---|---|---|---|
| $Ca^{2+}$ | .09* | .44 | 1.21 |
| $Co^{2+}$ | <0.01 | <0.02 | <0.02 |
| $Cu^{2+}$ | <0.03 | <0.02 | <0.02 |
| $Fe^{2+}$ | <0.03 | <0.03 | <0.03 |
| $Mg^{2+}$ | 0.25 | 0.30 | 0.49 |
| $Mn^{2+}$ | <0.01 | <0.01 | <0.01 |
| $Sr^{2+}$ | <0.05 | <0.03 | <0.03 |
| $Zn^{2+}$ | 0.05 | 0.01 | <0.01 |
| Total $M^2$ | <0.53 | <0.86 | <1.82 |

Thrombofax is the registered trademark of Ortho Diagnostics, Raritan, NJ. Actin and Actin-FS are the registered trademarks of American Dade, Miami, FL.
*Metal ion to ellagic acid molar concentration ratio. Ellagic acid concentration at 100 micromolar.

U.S. Pat. No. 4,732,860 to Bartl teaches a process using ellagic acid, preferably present at between 1.3 micromolar and 1.5 micromolar in combination with a phospholipid, including a cephalin to determine prekallikrein content and partial thromboplastin time. When these values are to be determined simultaneously, calcium ions are an essential ingredient in the process as they are integrally involved in the clotting process. Preferable calcium concentrations are taught to be 25,000 to 40,000 micromolar but may range from 1000 micromolar to 100,000 micromolar, some 769 to 76,923 times the ellagic acid concentration. When used, calcium ion is subsequent to the addition of a first reagent to the plasma sample.

The difficulty encountered with certain presently commercially available partial thromboplastin time reagents (APTT reagents) is that they often take a long time to prepare, a manufacturing drawback which increases expense. Further, these ellagic acid suspensions are not stable. With time ellagic acid may precipitate from the solution so that such reagents must be shaken before use. More preparation time is then required and the technician must be alert to the presence of precipitated ellagate compounds. As a result, the APTT test using these reagents is often unreproducible over a prolonged period of time. Another disadvantage in these presently available reagents is that they are typically not broadly factor selective. Although several factor sensitive reagents are available, the range of factors independently measured in narrow.

U.S. Pat. No. 3,486,981 to Speck teaches a partial thromboplastin time test reagent consisting of ellagic acid as the chemical activator of the Hageman factor. This patent contains no suggestion of the importance of divalent metal ions in promoting ellagic acid activity.

A paper by Bock et al, *Activation of Intrinsic Blood Coagulation by Ellagic Acid: Insoluble Ellagic Acid-Metal Ion Complexes Are the Activating Species*, Biochemistry (1981), 20, 7258–7266, teaches the importance of divalent metal ions, most significantly copper, in ellagic acid activation. This article teaches that soluble ellagic acid does not initiate blood coagulation. Instead insoluble ellagate:metal ion complexes are responsible for such activity. The authors conclude that previously reported ellagic acid activity as a factor in blood coagulation was based on the presence of adventitious metal ions most likely introduced into those solutions in the diluting buffer. Concentrations of ellagic acid investigated for procoagulant activity in the article were 30 micromolar more or less. Higher concentrations of ellagic acid were required in absolute solubility testing but not for efficiency testing. The authors demonstrated ellagic acid activity at these low ellagic acid concentrations upon addition of certain metal ions, namely $Cu^{2+}$, $Zn^{2+}$, $Co^{2+}$, and $Fe^{3+}$. The authors also used calcium and magnesium but found that these two ions demonstrated weaker affinity for ellagic acid and thus, according to the authors, were not preferred as ellagic acid activators. Further, the procedure for ellagic acid preparation resulted in precipitation after overnight incubation at concentrations as low as 20 micromolar ellagic acid in the presence of divalent metal ions. Metal ion concentration ratios were 1.5 or less relative to ellagic acid.

None of these references teaches the fundamental principle of the present invention: a stable ellagic acid:-cephalin:metal ion suspension wherein the metal ion species are present at molar ratios between 3 and 30 relative to the ellagic acid concentration. Further, none of these references teaches a stable reagent capable of forming a procoagulation reagent upon exposure to a source of cephalin containing ellagic acid at concentrations greater than 30 micromolar where divalent metal ion species are present at molar ratios of about 3.0 or less relative to the ellagic acid concentration.

SUMMARY OF THE INVENTION

A partial thromboplastin time reagent containing ellagic acid or an ellagic acid salt, such as sodium ellagate, at a predetermined preferred molar concentration, a molar ratio concentration between 3 and 30 relative to the ellagic acid or ellagic aicd salt, but preferably between about 4 and about 10 of a divalent metal ion or a mixture of divalent metal ions and a cephalin, which reagent exhibits improved activity and stability, is factor sensitive depending upon the divalent metal ion chosen. The divalent metal ions can be selected from the group consisting of magnesium, calcium, copper, cobalt, iron, lead, manganese, strontium, and zinc.

In another embodiment of the present invention a reagent capable of forming a procoagulation reagent upon exposure to a source of cephalin contains ellagic acid or an ellagic acid salt, such as sodium ellagate, at a predetermined optimum concentration and a divalent metal ion or a mixture of divalent metal ions in a molar ratio concentration of 3 or less, but at least 0.1, preferably 2 or less, but at least 0.5, to the ellagic acid or ellagic acid salt. The divalent metal ions can be selected from the above group and are preferably of low relative toxicity.

A further embodiment of the present invention is a method for making the above factor sensitive reagent for measuring partial thromboplastin time which requires the sequential steps of preparing a basic ellagic acid solution, adding an appropriate quantity of cephalin to the solution, followed by addition of a divalent metal ion in the appropriate molar ratio after an interval of time.

A method for making the reagent capable of forming a procoagulation reagent is also an embodiment of the present invention. In this method the following steps are performed sequentially. The ellagic acid is dissolved in a basic aqueous solution. A divalent metal ion is added to the solution in such amounts to form the appropriate molar ratio to the ellagic ion concentration of the reagent solution.

It is an object of the present invention to provide a partial thromboplastin time reagent capable of relatively short manufacturing time.

It is also an object to provide a partial thromboplastin time reagent with improved activity.

It is a further object of the present invention to provide a partial thromboplastin time reagent which has improved stability.

A further object of the present invention is to provide a partial thromboplastin time reagent which is factor selective.

Still another object of the present invention is to provide a factor sensitive partial thromboplastin time reagent which poses a minimized health risk to the medical technician.

Another object of the present invention is to provide a partial thromboplastin time reagent with improved reliability.

An additional object of the present invention is to provide a stable reagent capable of forming a procoagulation reagent upon exposure to a source of cephalin.

Still a further object of the present invention is to provide a platelet factor reagent.

Another object of the present invention is to provide a method for preparing the above factor sensitive partial thromboplastin time reagent.

A still further object of the present invention is to provide a method for preparing the above platelet factor reagent.

Additional objects and advantages will become apparent from the following descriptions.

DESCRIPTION OF THE PREFERRED EMBODIMENT

The APTT reagent of the present invention overcomes difficulties with previously available APTT reagents. In manufacturing, the reagent of the present invention may be speedily prepared since the ellagic acid concentration is actively enhanced by addition of a preferred concentration of divalent metal ions. Secondly, the reagent of the present invention has an extended shelf life. The ellagic acid remains suspended longer, improving the efficiency of the reagent. Increased shelf life of the stable suspension lends reliability to results obtained in optical instrument methods. The reagent is also factor selective depending upon the divalent metal ion chosen.

Moreover, an effective platelet factor reagent is previously unknown. Often, platelet viability is of concern. For example, certain leukemic states are characterized by large platelets, a relatively high percentage of which are nonfunctional in coagulation, perhaps due to absence of cephalin, a necessary factor in fibrin formation. Addressing this need, a platelet factor reagent is disclosed herein.

For the purposes of promoting an understanding of the principles of the invention, reference will now be made to the embodiments and specific language will be used to describe the same. It will nevertheless be understood that further applications of the principles of the invention as illustrated therein are contemplated as would normally occur to one skilled in the art to which the invention relates.

In accordance with the above summary the applicant has discovered ellagic acid activity, as measured by coagulation activation, is improved by the addition of a preferred relative amount of divalent metal ions. This amount is approximately four moles of divalent metal ion species to one mole of ellagic acid. At this concentration enough metal ions are present to form bridges between ellagic acid molecules and cephalin, but without causing precipitation. If the metal ion concentration is too low there are insufficient metal ions to coordinate with the ellagic acid present resulting in poor coagulation activation at neutral or alkaline pH. If no metal ions are present in solution, ellagic acid is completely ineffective as a prothrombin activator. Interestingly, if the metal ion concentration becomes too high the ellagic acid:cephalin:metal ion complex precipitates and no ellagic acid is left in solution to activate thromboplastin formation. In this regard, the applicant has found that the preferred ratio of divalent metal ions to ellagic acid is approximately 4 moles of divalent metal ion to one mole of ellagic acid. For example, if ellagic acid concentration is 0.1 mM then the divalent ion concentration should be between 0.7 mM and 0.3 mM, preferably approximately 0.4 mM. Surprisingly, this metal ion concentration is approximately the molar equivalent ratio of ellagic acid. Accordingly, the applicant has made an ellagic acid suspension which is more stable then has previously been reported. A slight excess of metal ion should be present to account for any competition for metal ions from other reagent components. On the whole, the divalent metal ions may be present in a ratio of between 3 and 30 relative to the ellagate ion; however, the ratio of divalent metal ions is preferably in a ratio of between about 4 and about 10.

Phospholipid concentration must be accounted for as a reagent component in determining the metal ion concentration. Phospholipids have some affinity for divalent metal ions. Cephalin, a phospholipid, is the common platelet substitute in APTT reagents. Cephalin concentration is also critical to the activity of the mixture as a procoagulant. The applicant has discovered that when the ellagic acid concentration is approximately 0.1 mM, cephalin should be present at approximately 1 mg ml$^{-1}$. Cephalin is available from several sources. A common source is rabbit brains. Soybeans are another source and perhaps, because of cost and other concerns, preferred. Soybean cephalin is available as AsolectinT from Associated Concentrates of Long Island, N.Y.

Before addition of the selected metal ion, the reagent solution may be assayed to determine the inherent metal ion concentration. Then the amount of metal ion added can be adjusted so that the final metal ion concentration is within the desired range. Assay procedures are well known in the art and the appropriate assay should be readily apparent to anyone skilled in the art. One such method utilizes atomic absorbtion spectroscopy.

Moreover, by selecting the divalent metal ion used, the applicant has discovered that reagents selective for different coagulation factors may be made. For example, if magnesium ion is used, the reagent becomes sensitive to the presence or absence of factors like Factor X and lupus coagulation inhibitor. Not all divalent metal ions are effective. Applicant's studies have shown that barium is ineffective and calcium, at the required high concentration, tends to precipitate the ellagic acid:cephalin:metal ion complex. Calcium also tends to detune the reagent rather than enhance factor sensitivity. Additionally, if two or more divalent metal ions create similarly factor sensitive reagents, the ion showing the least toxicity to humans may be chosen, thus reducing health risks for the laboratory technician.

Another embodiment of the present invention is a reagent capable of forming a procoagulant reagent upon exposure to a source of cephalin, i.e. a procoagulant precursor reagent. This reagent may be used, for example, to determine platelet factor by exposure to cephalin from platelets. At low molar ratios of divalent metal ion to ellagic acid the suspension becomes stable to prolonged storage, even in the absence of cephalin. The reagent produced contains about one-fourth the molar ratio of the divalent metal ions, or about 0.1 millimolar divalent ions for 0.1 millimolar ellagate ion. The metal ion species may be present up to 0.3 millimolar when the ellagic acid concentration is 0.1 millimolar; however concentrations below 0.2 are preferred and a concentration of about 0.05 mM is more preferred. At this relative concentration the reagent is stable to storage without the addition of cephalin. Then, upon the addition of a potential cephalin source to the reaction mixture, cephalin activity may be measured.

In the case of a platelet factor reagent, a plasma sample containing platelets is obtained from centrifuging whole blood at a slower rate than the rate necessary to obtain just plasma. This rate is well known to those of ordinary skill in the art and is 500 relative centrifugal force (rcf), more or less. The larger cellular materials such as whole cells fall out of the sample, leaving the smaller cellular materials like platelets suspended in the plasma. Addition of the plasma to the platelet factor reagent allows the coagulation activity of platelets to be measured as a function of cephalin activity. The less viable the platelets, the longer the clotting time upon addition of calcium.

Phenol may be used as a preservative and to inhibit bacterial growth in the reagent. Other common preservatives may also be used.

N-2-hydroxyethylpiperazine-$N_1$-2-ethanesulfonic acid (HEPES) hemisodium salt is an effective buffering material for maintaining the desired pH, typically about 7.4. Other buffers, readily known to those of ordinary skill in the art, may also be used.

An APTT reagent made according to the present invention is also useful in coagulation determinations which do not use optic instruments. In these methods the APTT reagent and the plasma samples are added to a test tube and the time for clot formation after a calcium reagent is added is determined by visual observation and compared to normal and abnormal coagulation control samples. Such a method is described in more detail in Example 6 below.

A further embodiment of the present invention involves a method for making the factor sensitive APTT reagent described above. In making the factor sensitive APTT reagent it is important that the components be added in a specific order and, between some additions, sufficient time elapse for the solutes to react. The following is a general description of the method. More detail is found in the Examples below. The ellagic acid or an ellagic acid salt is dissolved in a basic aqueous solution to the desired concentration. The ellegate solution is sonicated and allowed to stand for 30 minutes and diluted and pH adjusted to 7.3±0.1 and allowed to stand one or more hours, preferrably 48 hours. To the ellagate solution, cephalin is added, and this resulting solution is allowed to stand for 30 minutes, more or less. Then, the appropriate quantity of divalent metal ion species is added. The final step is addition of a buffer to maintain the desired pH, a pH of about 7.5 is preferred.

Procoagulant precursor reagent is made according to the above method; however, cephalin is not added.

Exact adherence to the sequence in performing the above steps is of critical importance to practice the present invention. Upon experimentation, applicant surprisingly discovered that any modifications of the sequence dramatically affect the stability of the present invention. For example, should the metal ion be added to the ellagic acid solution before the addition of the cephalin, rather than as the last step of the procedure, the ellagic acid:cephalin:metal ion complex does not become optimally active. Thus it is crucial in practicing the present invention with the heretofore unknown high metal ion concentrations that the reagent components be added in the order described above.

Reference will now be made to specific examples for the purpose of further describing and understanding the features of applicant's preferred embodiments as well as their advantages and improvements over the art. In this regard, where possible, specific reference has been made in the examples to known prior art processes in order to better understand and distinguish applicant's invention herein. It is further understood that these examples are representative only and that such additional embodiments and improvements of the same are within the contemplation and scope of applicant's invention as would occur to someone of ordinary skill in this art.

EXAMPLE 1

Preparation of APTT Reagent

1. Approximately 24 grams of phenol is weighed and transferred to a clean 6 liter container. $5.0 \pm 0.01$ liters of 18 megohm/cm reagent water is added and the phenol is stirred until completely dissolved.

2. $4.0 \pm 0.01$ grams of sodium hydroxide is separately dissolved in 1 liter of 18 megohm/cm water. The sodium hydroxide concentration of this solution is 0.1M.

3. $0.17 \pm 0.001$ grams of ellagic acid recrystallized from pyridine is weighed into a 100 ml glass beaker. 25 ml of the above 0.1 molar sodium hydroxide solution is added to the beaker containing ellagic acid. The ellagic acid may be aided in dissolution by sonication. The solution is allowed to stand for 30 minutes.

4. The resulting ellagic acid solution is quantitatively transferred to the phenol solution and mixed for 10 minutes, while the pH is adjusted to $7.3 \pm 0.1$ with acid, such as N-2-hydroxyethylpiperazine-$N_1$-2-ethanesulfonic acid (HEPES). This ellagic acid/phenol/sodium hydroxide solution is allowed to stand at ambient temperature for 48 hours, more or less.

5. In the meantime, $6.2 \pm 0.1$ grams of HEPES hemisodium salt is weighed and dissolved in 500 ml of 18 megohm/cm water.

6. $5.0 \pm 0.1$ grams Asolectin TM (soybean cephalin) is placed in a Waring blender and 100 ml of the HEPES buffer is added. Alternatively, cephalin from rabbit brains is an excellent alternative.

7. The mixture is blended for 2 minutes before adding the remaining 400 ml of HEPES buffer and further blending for 1 minute.

8. The resulting cephalin mixture is strained through glass wool into the ellagic acid solution with stirring for 5 minutes.

9. After 30 minutes have elapsed 10 ml of a 0.2 molar manganese chloride solution is added so that the final concentration is approximately 400 $\mu$M manganese ion.

10. Finally, $31.2 \pm 0.1$ grams of HEPES hemisodium salt is weighed out and added to the reagent solution. This solution is stirred for 10 minutes.

The resulting reagent was used in an APTT test with satisfactory results.

EXAMPLE 2

Preparation of APTT Reagent Sensitive to Factor X and Lupus Coagulation Inhibitor The procedure in Example 1 is followed except that 10 ml of 0.2M magnesium chloride is substituted for 10 ml of 0.2M manganese chloride again with a resulting final concentration of 400 $\mu$M magnesium ion. The resulting reagent was used in APTT testing with satisfactory results including increased sensitivity to Factor X and Lupus coagulation inhibitor.

EXAMPLE 3

Preparation of Platelet Factor Reagent

The procedure of Example 1 is followed except that cephalin is not added to the reagent mixture. Also, only 1.25 ml of 0.2M magnesium chloride is added so that the final molar concentration is 1 mM magnesium or less, preferably 50 $\mu$M in the present example, and preferably 10 $\mu$M or more. The resulting reagent was used to determine platelet deficiency with satisfactory results.

EXAMPLE 4–6

The reagents of Examples 1–3 are prepared with the additional step of assaying the metal ion concentration by atomic absorbtion spectroscopy. Then the ultimate metal ion concentration is adjusted by adding a sufficient quantity so that when added to the metal ion concentration already present, the intended final specific metal ion concentration is achieved.

EXAMPLE 7

Determination of Activated Partial Thromboplastin Time Using an Optical Instrument The following Example is adapted from the procedure outlined in the operation manual for the Electra 750 Plasma Coagulation Timing Instrument available from MLA. Standard good laboratory practice procedures should be followed in coagulation time testing in order to obtain good results. These good laboratory practice procedures are known to a technician ordinarily skilled in the art. This method is sensitive to all coagulation factors except Factors VII, XIII and platelets.

1. Blood obtained from a vein is centrifuged after addition of 3.8% sodium citrate or 0.1M sodium oxalate at 1 part for ever 9 parts whole blood, to separate the plasma. The supernatant plasma is removed from the precipitated cells. Centrifugation at 1000 rcf for 6 minutes is recommended. The specimens should be kept cold and should be tested as soon as possible. At the latest all plasma should be tested within 4 hours of being drawn.

2. Add 0.1 ml of the reagent prepared according to Example 1 above and 0.1 ml of the plasma to a test tube. Shake the mixture and place in a 37° bath for approximately 300 seconds.

3. After 300 seconds passes place the sample in the sample test station of the Electra 750 Optical Instrument.

4. Add 0.1 ml of 0.02M calcium chloride and begin the instrument timer.

5. When the timer stops the clock time is recorded. The timer stops when the sample clots thus indicating the clot time.

6. A normal and abnormal coagulation control sample should be included in each series of tests run in order to validate the reliability of the test results.

Prolongation of the clot time is indicative of a deficiency or abnormality in one of the clotting factors, information useful in medical diagnosis and treatment. Generally, when the above procedure is used clot time is between 25 and 45 seconds. Activated partial thromboplastin time measured in this manner should be accurate within a variation of 1.3%. Clot times were satisfactorily determined according to this method.

EXAMPLE 8

Determination of Platelet Factor

The procedure of Example 4 is followed except that the plasma sample is spun at approximately 500 rcf before the platelet containing plasma is decanted from the precipitate. In addition, the reagent made according to Example 2 above is substituted for the reagent made in Example 1. A long clotting time may indicate a deficiency in the sample platelets. However, the test results must be interpreted in conjunction with other results. For example, if the test performed according to Example 4 indicates a normal clotting time but the clot time is slow under the procedure described in this Example, the platelets are likely defective. Information about platelet deficiency is useful in medical treatment and diagnosis. Clot times were satisfactorily determined with this method.

EXAMPLE 9

Measurement of Activated Partial Thromboplastin Time Without the use of an Optical Instrument The following procedure may be used to determine activated partial thromboplastin time without the use of an optical instrument.

1. Venous blood is obtained and immediately mixed in a ratio of 9 parts whole blood to 1 part anticoagulant. 0.1M sodium citrate solutions are acceptable anticoagulants.

2. Within 30 minutes of drawing the blood, the sample is centrifuged at approximately 1000 rcf for 15 minutes. The supernatant plasma is decanted. The plasma may be stored up to 2 hours at 2–8° C.

3. 0.1 ml of APTT reagent made according to Example 1 is pipetted into a 10×75 mm test tube, along with 0.1 ml of the plasma sample. The solution is incubated for 3 minutes at 37° C.

4. 0.1 ml of 0.02M 37° calcium chloride is added to the solution and simultaneously a timer is started.

5. When a clot is observed by the eye, the timer is stopped and the time elapsed from the addition of the calcium chloride is noted.

6. Normal and abnormal coagulation control should be included in each series of samples in order to validate the reliability of the test results.

7. Normal coagulation time varies according to age and sex of the subject but, in general, a normal range is 26 to 34 seconds.

The information regarding clot time acquired according to the above method is useful in certain medical diagnosis and treatment. Clot times were determined by this method with satisfactory results.

What is claimed is:

1. A stable factor sensitive reagent for measuring partial thromboplastin time comprising:
    ellagic acid or a ellagic acid salt present at a predetermined molar concentration;
    a divalent metal ion, said divalent metal ion present at a molar ratio between 3 and 30 to said ellagic acid or ellagic acid salt; and,
    a cephalin.

2. The reagent of claim 1 wherein the molar ratio of said divalent metal ion to said ellagic acid or ellagic acid salt is between about 4 and about 10.

3. The reagent of claim 2 wherein said ellagic acid or ellagic acid salt is sodium ellagate.

4. The reagent of claim 2 wherein said cephalin is soybean cephalin.

5. The reagent of claim 2 wherein said divalent metal ion is selected from the group consisting of:
    magnesium;
    calcium;
    copper;
    cobalt;
    iron;
    lead;
    manganese;
    strontium; and,
    zinc.

6. The reagent of claim 5 wherein said divalent metal ion is manganese.

7. The reagent of claim 5 wherein said divalent metal ion is magnesium.

8. The reagent of claim 1 wherein the predetermined molar concentration is approximately 0.1 millimolar.

9. The reagent of claim 8 and further wherein the divalent metal ion concentration is between 0.7 millimolar and 0.3 millimolar.

10. A stable factor sensitive reagent for measuring partial thromboplastin time comprising:
    ellagic acid or an ellagic acid salt present at a predetermined molar concentration;
    divalent metal ions, said divalent metal ions present at a molar ratio between 3 and 30 to said ellagic acid or ellagic acid salt; and,
    a cephalin.

11. The reagent of claim 10 wherein the molar ratio of said divalent metal ions to said ellagic acid or ellagic acid salt is between about 4 and about 10.

12. The reagent of claim 11 wherein said ellagic acid or ellagic acid salt is sodium ellagate.

13. The reagent of claim 11 wherein said divalent metal ions are selected from the group consisting of:
    magnesium;
    calcium;
    copper;
    cobalt;
    iron;
    lead;
    manganese;
    strontium; and
    zinc.

14. The reagent of claim 13 wherein said divalent metal ions include manganese.

15. The reagent of claim 13 wherein said divalent metal ions include magnesium.

16. The reagent of claim 10 wherein the predetermined molar concentration is approximately 0.1 millimolar.

17. The reagent of claim 16 and further wherein the concentration of divalent metal ions is between 0.7 millimolar and 0.3 millimolar.

18. The reagent of claim 10 wherein said cephalin is soybean cephalin.

19. A stable reagent capable of forming a procoagulation reagent upon exposure to a source of cephalin consisting essentially of:
ellagic acid or an ellagic acid salt present at a predetermined molar concentration; and,
a divalent metal ion, said divalent metal ion present at a molar ratio of 3 or less, but greater than 0.1, to said ellagic acid or ellagic acid salt.

20. The reagent of claim 19 wherein the molar ratio of said divalent metal ion to said ellagic acid or ellagic acid salt is 2 or less but greater than 0.5.

21. The reagent of claim 20 wherein said divalent metal ion is selected from the group consisting of:
magnesium;
calcium;
copper;
cobalt;
iron;
lead;
manganese;
strontium; and,
zinc.

22. The reagent of claim 20 wherein the divalent metal ion is of low relative toxicity.

23. The reagent of claim 19 wherein said ellagic acid or ellagic acid salt is sodium ellagate.

24. The reagent of claim 19 wherein the predetermined molar concentration of ellagic acid or ellagic acid salt is approximately 0.1 millimolar.

25. The reagent of claim 24 and further wherein the divalent metal ion concentration is approximately 0.05 millimolar.

26. The reagent of claim 19 wherein said divalent metal ion is selected from the group consisting of:
magnesium;
calcium;
copper;
cobalt;
iron;
lead;
manganese;
strontium; and,
zinc.

27. The reagent of claim 26 wherein the divalent metal ion is magnesium.

28. A stable reagent capable of forming a procoagulation reagent upon exposure to a source of cephalin consisting essentially of:
ellagic acid or an ellagic acid salt present at a predetermined molar concentration; and,
divalent metal ions, said divalent metal ions present at a molar ratio of 3 or less, but greater than 0.1, to said ellagic acid or ellagic acid salt.

29. The reagent of claim 28 wherein the molar ratio of said divalent metal ions to said ellagic acid or ellagic acid salt is 2 or less but greater than 0.5.

30. The reagent of claim 29 wherein said ellagic acid or ellagic acid salt is sodium ellagate.

31. The reagent of claim 29 wherein said divalent metal ions are selected from the group consisting of:
magnesium;
calcium;
copper;
cobalt;
iron;
lead;
manganese;
strontium; and,
zinc.

32. The reagent of claim 28 wherein the predetermined molar concentration of ellagic acid or ellagic acid salt is approximately 0.1 millimolar.

33. The reagent of claim 32 and further wherein the concentration of divalent metal ions is approximately 0.05 millimolar.

34. The reagent of claim 28 wherein said divalent metal ions are selected from the group consisting of:
magnesium;
calcium;
copper;
cobalt;
iron;
lead;
manganese;
strontium; and,
zinc.

35. The reagent of claim 34 wherein the divalent metal ions include magnesium.

36. The reagent of claim 34 wherein the divalent metal ions are of low relative toxicity.

37. A method of making a stable factor sensitive reagent for measuring partial thromboplastin time comprising the sequential steps of:
first, dissolving a known weight of an ellagic acid or an ellagic acid salt in an aqueous solution;
second, adding a cephalin to the above resulting solution;
third, adjusting the concentration of divalant metal ions of said solution to achieve a divalent metal ion molar ratio between 3 and 30 relative to the ellagic acid or ellagic acid salt of said solution; and,
fourth, adjusting the pH of the resulting ellagic acid solution to approximately 7.5.

38. The method of claim 37 and further comprising assaying one or more of said cephalin, said ellagic acid or ellagic acid salt, or said aqueous solution prior to said adjusting the divalent metal ion concentration.

39. The method of claim 38 wherein said assaying is accomplished by atomic absorbtion spectroscopy.

40. The method of claim 37 wherein said ellagic acid or ellagic acid salt is sodium ellagate.

41. The method of claim 37 wherein the final molar concentration of ellagic acid or ellagic acid salt in the reagent is approximately 0.1 millimolar.

42. The method of claim 37 wherein said divalent metal ions are selected from the group consisting of:
magnesium;
calcium;
copper;
cobalt;
iron;
lead;
manganese;
strontium; and,
zinc.

43. The method of claim 37 wherein the cephalin is soybean cephalin.

44. The method of claim 37 wherein said adjusting of the pH of said solution is accomplished by addition of a buffer.

45. The method of claim 44 wherein the buffer is N-2-hydroxyethylpiperazine-$N_1$-2-ethanesulfonic acid hemisodium salt.

46. A method of making a stable reagent capable of forming a procoagulation reagent upon exposure to a source of cephalin comprising the sequential steps of:
  first, dissolving a known weight of an ellagic acid or an ellagic acid salt in an aqueous solution;
  second, adjusting the concentration of divalent metal ions of said solution to achieve a divalent metal ion molar ratio of about 3 or less, but at least 0.1, relative to the ellagic acid or ellagic acid salt of said solution; and,
  third, adjusting the pH of the resulting ellagic acid solution to approximately 7.5.

47. The method of claim 46 and further comprising assaying one or more of said ellagic acid or ellagic acid salt or said aqueous solution prior to said adjusting the divalent metal ion concentration.

48. The method of claim 47 wherein said assaying is accomplished by atomic absorbtion spectroscopy.

49. The method of claim 46 wherein said ellagic acid or ellagic acid salt is sodium ellagate.

50. The method of claim 46 wherein the final molar concentration of ellagic acid or ellagic acid salt in the reagent is approximately 0.1 millimolar.

51. The method of claim 46 wherein said divalent metal ions are selected from the group consisting of:
  magnesium;
  calcium;
  copper;
  cobalt;
  iron;
  lead;
  manganese;
  strontium; and,
  zinc.

52. The method of claim 46 wherein said adjusting of the pH of said solution is accomplished by addition of a buffer.

53. The method of claim 52 wherein the buffer is N-2-hydroxyethylpiperazine-$N_1$-2-ethanesulfonic acid hemisodium salt.

* * * * *